United States Patent [19]

Huffman et al.

[11] Patent Number: 5,403,301

[45] Date of Patent: * Apr. 4, 1995

[54] DISPOSABLE ABSORBENT GARMENT WITH COMPOSITE TOPSHEET ASSEMBLY

[75] Inventors: Gloria Huffman, Kent; Heinz A. Pieniak, Des Moines, both of Wash.

[73] Assignee: Paragon Trade Brands, Inc., Federal Way, Wash.

[*] Notice: The portion of the term of this patent subsequent to Jan. 4, 2011 has been disclaimed.

[21] Appl. No.: 177,246

[22] Filed: Jan. 4, 1994

Related U.S. Application Data

[63] Continuation-in-part of Ser. No. 608,809, Nov. 5, 1990, Pat. No. 5,275,590.

[51] Int. Cl.$^6$ .............................................. A61F 13/15
[52] U.S. Cl. .............................. 604/385.2; 604/385.1
[58] Field of Search ................... 604/358, 385.1, 385.2

[56] References Cited

U.S. PATENT DOCUMENTS

| | | |
|---|---|---|
| 4,636,207 | 1/1987 | Buell . |
| 4,681,579 | 7/1987 | Toussant . |
| 4,695,278 | 9/1987 | Lawson . |
| 4,704,116 | 11/1987 | Enloe . |
| 4,795,454 | 1/1989 | Dragoo . |
| 4,813,947 | 3/1989 | Korpman . |
| 4,816,025 | 3/1989 | Foreman . |
| 4,822,435 | 4/1989 | Igaue . |
| 4,861,635 | 8/1989 | Carpenter . |
| 4,892,528 | 1/1990 | Suzuki . |
| 4,904,251 | 2/1990 | Igaue . |
| 5,021,051 | 6/1991 | Hiuke . |
| 5,064,489 | 11/1991 | Ujimoto . |
| 5,080,658 | 1/1992 | Igaue . |
| 5,085,654 | 2/1992 | Buell . |
| 5,275,590 | 1/1994 | Huffman et al. ............... 604/385.2 |

FOREIGN PATENT DOCUMENTS

| | | |
|---|---|---|
| 0109126 | 11/1983 | European Pat. Off. . |
| 0337969 | 4/1989 | European Pat. Off. . |
| 0386815 | 2/1990 | European Pat. Off. . |

Primary Examiner—Randall L. Green
Assistant Examiner—Mary Beth Jones
Attorney, Agent, or Firm—Dressler, Goldsmith, Shore & Milnamow, Ltd.

[57] ABSTRACT

A disposable absorbent garment, illustrated as a disposable diaper, includes a backsheet, an absorbent panel positioned on top of the backsheet, and a composite, three-component topsheet assembly positioned on top of the absorbent panel. The topsheet assembly includes a central portion generally overlying the absorbent panel, and a pair of side marginal portions joined to opposite side edges of the central portion. Each side marginal portion includes a plurality of segments, including an elasticized, standing gather segment for enhanced containment. The containment characteristics of the garment are further enhanced by joining the central portion of the topsheet assembly to each side marginal portion in spaced relationship to the associated backsheet of the garment.

4 Claims, 3 Drawing Sheets

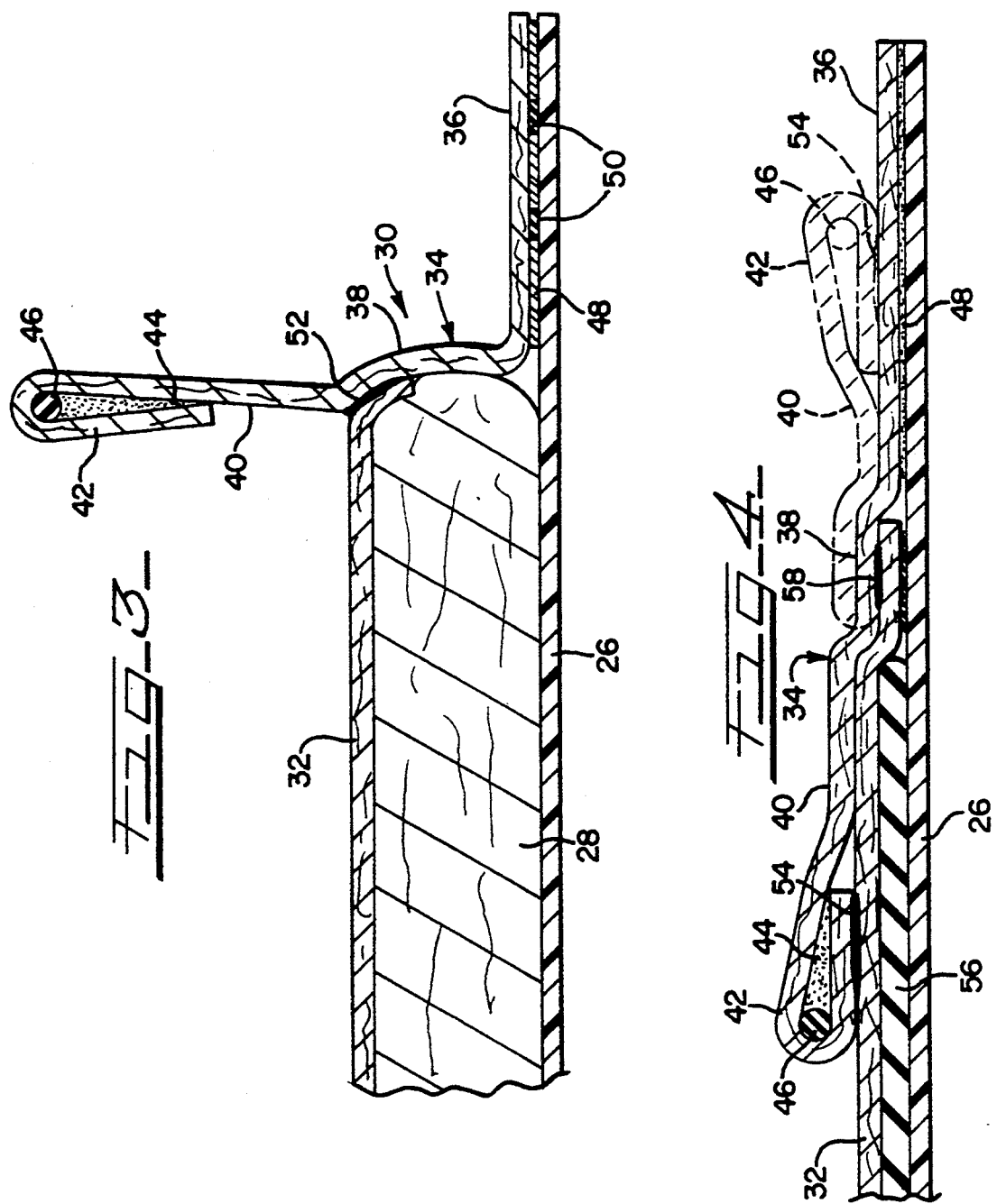

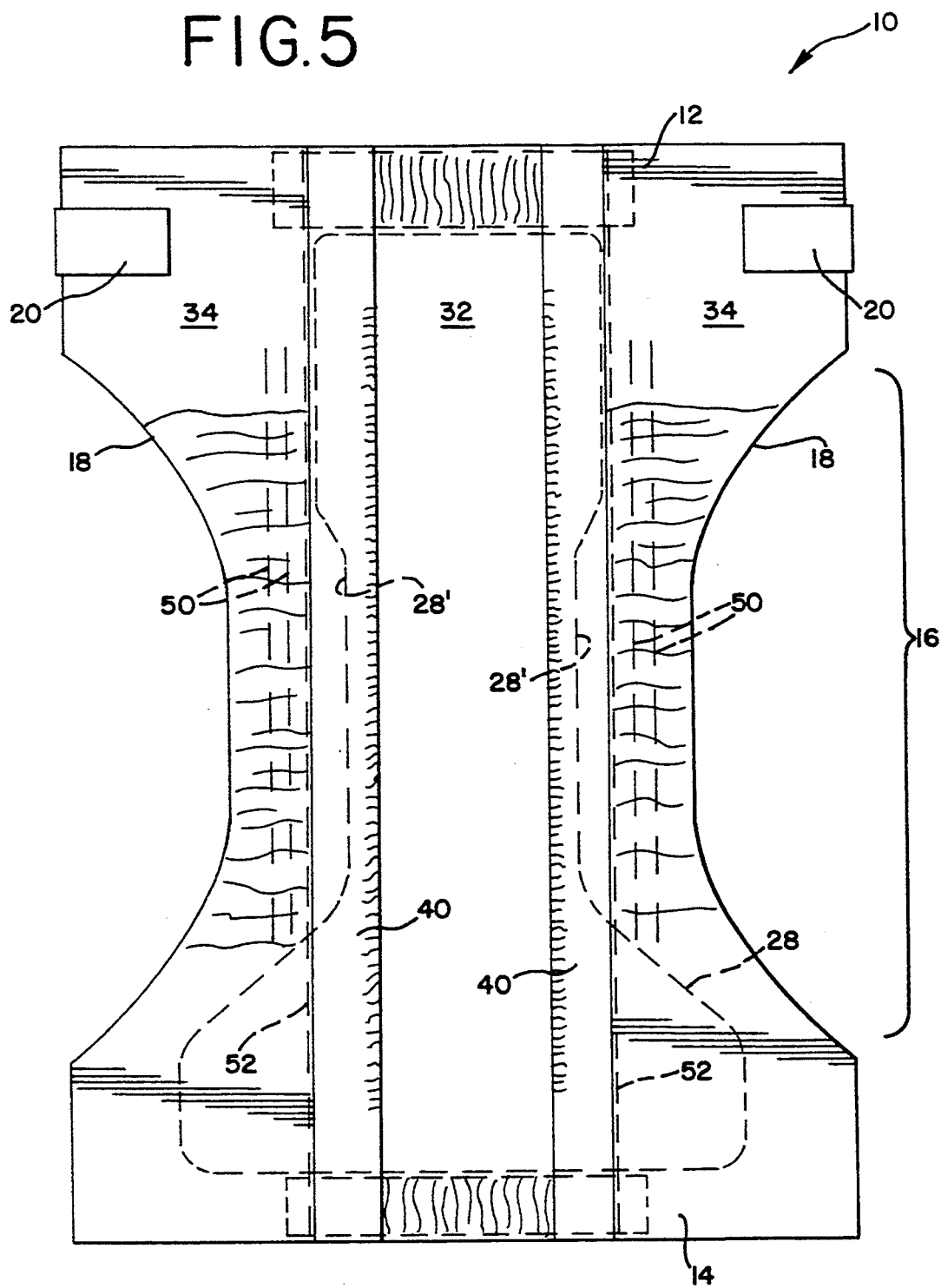

DISPOSABLE ABSORBENT GARMENT WITH COMPOSITE TOPSHEET ASSEMBLY

CROSS-REFERENCE TO RELATED APPLICATION

This application is a continuation-in-part of U.S. patent application Ser. No. 07/608,809, filed Nov. 5, 1990, now U.S. Pat. No. 5,275,590, issued Jan. 4, 1994.

TECHNICAL FIELD

The present invention relates generally to disposable absorbent garments such as disposable diapers and the like, and more particularly to a disposable absorbent garment having a composite, three-component topsheet assembly providing enhanced containment characteristics.

BACKGROUND OF THE INVENTION

Disposable absorbent garments, such as disposable diapers and the like, have found wide spread acceptance for infant care. Garments of this nature are typically configured for single use, with an absorbent panel or core of the diaper ordinarily provided in an integrated structure including a moisture-pervious topsheet or facing layer, and a moisture-impervious backsheet or backing layer. Adhesive coated tape tabs are provided to facilitate convenient fitting of the diaper to a baby, with elastication of the garment, such as at the leg and waist openings, providing enhanced fit and comfort. Garments of this nature are not only suitable for infants, but can be appropriately sized and configured for incontinence use by adults.

As will be appreciated, the containment characteristics of a disposable absorbent garment are a key aspect of its overall performance. Elasticized disposable absorbent garments have enhanced containment characteristics, with the provision of elastic elements at both the leg openings and waist openings of a garment being particularly effective.

In addition to providing elastic elements adjacent the leg openings, it is known to provide an associated inwardly extending elasticized component, in the nature of a gather or flap, with such arrangements ordinarily positioned to overlap the associated absorbent panel. While this type of construction, sometimes referred to as an inner standing gather, desirably enhances containment by confining liquid and solid materials in the region above the absorbent panel for absorption, the specific configuration of such arrangements can greatly affect the containment characteristics.

In this regard, it is believed that the disposition of such an inner standing gather relative to the edge of the garment's absorbent panel has a significant effect on containment. Some products have inner standing gathers positioned so that the gathers each have a base portion disposed substantially inwardly of a respective side edge of the absorbent panel. In other words, the absorbent panel extends beneath the inner standing gathers, including in the longitudinally central, crotch area of the garment. However, depending upon the material from which the gather and diaper topsheet are formed, this construction may not provide the desired containment characteristics in that liquid absorbed into the absorbent panel can pass beneath the inner standing gathers, and leak from the leg openings of the garment.

It is further believed that the disposition of such inner standing gathers relative to the associated topsheet, overlying the absorbent panel, impacts on the effectiveness of such gathers. Specifically, some constructions in which the base portion of each gather is positioned beyond the respective side edge of the absorbent panel have the associated topsheet secured substantially directly to the backsheet of the garment, such as at the base of the inner standing gather. It is believed that the trough-like region thus defined just inside of each inner standing gather permits the collection or "puddling" of liquid in a manner which can result in the liquid being forced under, over, or through the inner standing gather, when the liquid is subjected to pressure during the usual wearing of the garment.

In accordance with the present invention, a disposable absorbent garment, illustrated in the form of a disposable diaper, has been particularly configured to provide a structure having inner standing gather elements configured to cooperate with associated components of the diaper for enhanced containment. This is achieved through the provision of a multi-component topsheet assembly, with components of the top of the assembly selected to exhibit the desired degree of liquid-permeability for effective absorption, while at the same time minimizing problems of strike-back or rewetting, as well as minimizing leakage from the garment.

SUMMARY OF THE INVENTION

A disposable absorbent garment embodying the principles of the present invention includes a composite, three-component topsheet assembly, which assembly is configured to include a pair of preferably hydrophobic inner standing gather constructions. When the topsheet assembly is integrated with the associated components of the absorbent garment, the resultant construction desirably minimizes leakage by abating the passage of liquid through the absorbent panel in the crotch area beneath the inner standing gathers.

Additionally, the composite topsheet assembly is configured to avoid the formation of trough-like recesses adjacent the inner standing gathers, thus abating leakage by precluding significant collection or "puddling" of liquid just inwardly of the standing gathers. The arrangement of the bonds of the components of the topsheet assembly acts in cooperation with the hydrophobic standing gathers to abate liquid movement past the standing gathers, either by movement through, beneath, or over the gathers. The gathers thus function in the nature of outer boundary elements to confine liquid within the absorbent article. This effect can be enhanced by configuring the absorbent panel of the article at least in the crotch area, to be substantially positioned between the standing gathers. The resultant absence of absorbent material beyond the gathers further contributes to the superior containment characteristics of the present construction.

In accordance with the illustrated embodiment, the present disposable absorbent garment includes a backsheet, which is preferably liquid-impermeable, and an absorbent panel positioned on top of the backsheet. The absorbent panel can be provided in any of a variety of forms, with absorbent matrices comprising combinations of comminuted wood pulp and superabsorbent polymeric materials being particularly preferred.

The present garment further includes a composite, three-component topsheet assembly positioned on top of the absorbent panel. The topsheet assembly includes a central portion which generally overlies the absorbent panel, and a pair of side marginal portions at respective opposite sides of the central portion. In a presently preferred form, the side marginal portions exhibit a significant degree of hydrophobicity and liquid impermeability, while the material of the central portion exhibits relatively greater hydrophilicity than the side marginal portions.

Each of the side marginal portions is characterized by three segments, which arrangement provides the desired containment characteristics for the product. In at least a crotch area of the garment, each side marginal portion includes a first segment juxtaposed and bonded to the backsheet of the garment laterally outwardly of the associated absorbent panel. Each side marginal portion further includes a second, intermediate segment adjacent the first segment, and a third standing gather segment adjacent the second intermediate segment.

In accordance with the illustrated embodiment, each standing gather segment includes an overturned free edge to thereby define a sleeve portion, with the garment including at least one elastic element extending within each of the sleeve portions along at least the crotch area of the garment. Additionally, at least one elastic element is preferably positioned between each of the first segments of the side marginal portions, and the juxtaposed backsheet, again at least in the crotch area of the absorbent garment. This arrangement provides desired elasticized leg openings of the garment.

The relative dispositions of the central and side marginal portions of the composite topsheet assembly have been particularly selected for enhanced performance. Specifically, the central portion of the topsheet assembly terminates at and is joined to each of the side marginal portions generally at the respective juncture of the second intermediate segment and the third standing gather segment. By this construction, the central portion is joined in spaced relationship, by the intermediate segment, to the backsheet at least in the crotch area of the absorbent garment. This configuration has been found to desirably avoid the formation of trough-like regions wherein liquid can collect and move past (i.e., through, beneath, or over) the standing gather constructions under the influence of pressure attendant to wearing.

In the illustrated embodiment, the absorbent panel is positioned substantially entirely inwardly of the base of each standing gather in the crotch area. Thus, there is no gap or spacing between the marginal portions and the backsheet through which liquid might otherwise leak.

While it is generally preferred that the absorbent panel be substantially confined inwardly of the standing gathers in the crotch area, the manner in which the central portion of the topsheet assembly is joined to each marginal portion in spaced relationship to the backsheet is believed to be particularly significant in abating leakage. Accordingly, a garment embodying the present invention may be configured such that the central portion is joined to each marginal portion at or just inwardly of the respective side edge of the absorbent panel. Even though a portion of the panel may thus extend beneath the standing gathers, the creation of trough-like regions is desirably avoided. This arrangement can be desirable in light of normal manufacturing tolerances, which can make it difficult to consistently position the bond at each edge of the central portion in precise alignment with the respective edge of the absorbent panel. Thus, particularly in the case of relatively thin absorbent panels, it can be desirable to join the central portion to each marginal portion at, or inwardly of, the respective edge of the absorbent panel.

In known arrangements, the side margins of a topsheet are typically formed from the same material as its central portion which can contribute to leakage. In significant distinction, the side marginal portions of the present construction can be selected for leakage resistance, while the central portion can be independently selected to exhibit the desired degree of permeability to permit liquid to move therethrough to the absorbent panel.

In the illustrated embodiment, the absorbent panel of the construction has a generally hourglass or I-shaped configuration, and thus defines a pair of laterally extending ear portions at each of the front and rear waist portions of the garment. In these portions, the absorbent panel extends beneath the standing gathers, but the preferred formation of the side marginal portions of the composite topsheet from hydrophobic material desirably minimizes any leakage from the ear portions. Additionally, the preferred use of hydrophobic material in these regions of the garment has been found to exhibit improved strength, and stretch and tear resistance attendant to use of the garment's adhesive tape tabs.

Other features and advantages of the present invention will become readily apparent from the following detailed description, the accompanying drawings, and the appended claims.

BRIEF DESCRIPTION OF THE DRAWINGS

FIG. 3 is a fragmentary, cross-sectional view taken along lines 3—3 of FIG. 2;

FIG. 4 is a fragmentary, cross-sectional view taken generally along lines 4—4 of FIG. 2; and FIG. 5 is a top plan view of a modified embodiment of the present invention.

DETAILED DESCRIPTION

Figure 1:
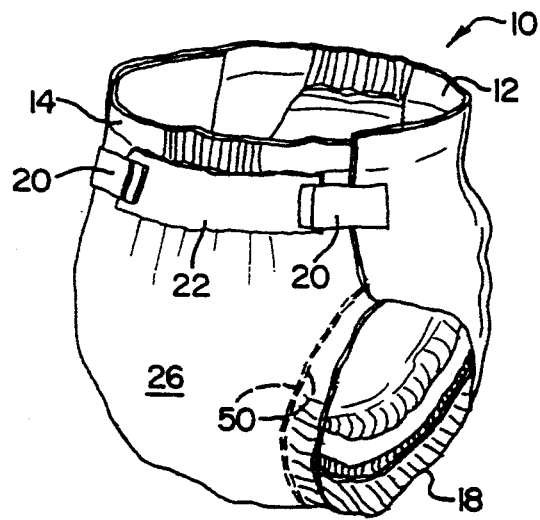
FIG. 1 is a perspective view of a disposable absorbent garment embodying the principles of the present invention illustrated generally as it appears when being worn.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to the drawings, therein is illustrated a disposable absorbent garment 10, illustrated as a disposable diaper, embodying the principles of the present invention. As used in the present disclosure, the term "diaper" is intended to refer to an absorbent garment which is worn by an individual for absorbing urine and/or fecal matter. It is to be understood that garments embodying the principles of the present invention can be appropriately sized for use by infants and children, and can further be sized for use by incontinent adults. Additionally, absorbent garments embodying the present invention may take the form of sanitary products, or absorbent diaper inserts.

Figure 2:
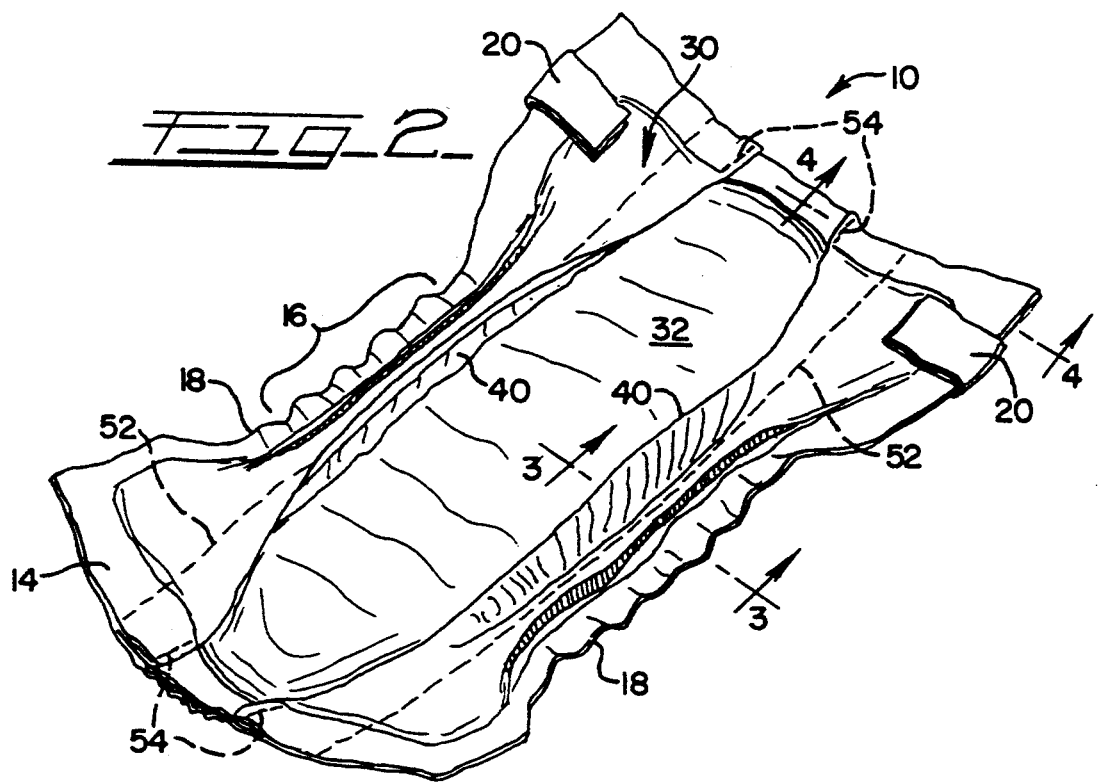
FIG. 2 is a top perspective view of the present absorbent garment generally in a form prior to use.

With particular reference to FIG. 2, absorbent garment 10 includes a rear waist portion 12, a front waist portion 14, and a crotch area 16 extending between the front and rear waist portions. The crotch area of the garment generally corresponds to that portion which is positioned between the legs of a wearer during use, and as used herein, comprises between about one-third and three-fourths of the longitudinally central portion of the garment.

For enhanced fit and comfort, garment 10 has a generally I-shaped, contoured configuration, with the crotch area 16 being relatively narrow by virtue of the formation of leg cut-outs 18 at each of the side margins of the garment.

Convenient securement of the absorbent garment 10 to a wearer is facilitated by the provision of a pair of adhesive-coated tape tabs 20 at respective opposite sides of the rear waist portion 12 of the garment. The tape tabs 20 are positioned for securement to the outside surface of the front waist portion 14, as illustrated in FIG. 1, and to this end, a tape landing zone 22 is preferably provided. Landing zone 22 typically comprises a strip of polymeric sheet material to which the tape tabs can be securely, yet removably applied, with the landing zone 22 desirably acting to reinforce the front outside surface of the garment so that removal and reapplication of the tape tabs 20 does not damage the garment.

With reference to FIGS. 2, 3, and 4, the absorbent garment 10 includes a preferably liquid-permeable backsheet 26 which generally defines the outer surface of the garment. The liquid impermeable characteristics of the backsheet act to prevent leakage of liquid through the backsheet for the desired containment characteristics. A wide variety of suitable polymeric film materials can be employed for the backsheet 26, such as a polyethylene sheet having a thickness on the order of 0.0005 to 0.001 inches. Polyethylene terephthalate sheet material having a thickness of approximately 0.0005 to 0.001 inches may alternately be employed. Nonwoven materials being exhibiting liquid-impermeability can be used, as can composite or laminate sheet materials such as comprising integrated nonwoven fabric and polymeric film layers.

Absorbent garment 10 further includes an absorbent panel 28 positioned on top of the backsheet 26. The absorbent panel preferably comprises an absorbent matrix including comminuted wood pulp, sometimes referred to as wood fluff, and superabsorbent material, which may comprise superabsorbent polymers or the like. Absorbent matrices comprising blends and/or layers of such absorbent materials can be employed. If desired, the superabsorbent material may be more heavily concentrated in specifically selected regions of the absorbent panel. Additionally, an absorbent matrix formed in accordance with U.S. Pat. No. 4,573,988, to Pieniak, comprising a compressed composite absorbent structure including a resilient web of fibers having superabsorbent material incorporated therein, can be used.

In accordance with the present invention, absorbent garment 10 includes a composite, three-component topsheet assembly 30 positioned on top of the absorbent panel 28. The three-component assembly includes a central liquid-permeable portion 32 which generally overlies the absorbent panel 28, and a pair of side marginal portions 34 joined to respective opposite side edges of the central portion 32.

As best shown in FIG. 3, each of the side marginal portions 34 of the topsheet assembly 30 includes a plurality of segments which, at least in the crotch area 16 of the diaper, are arranged relative to central portion 32 and absorbent panel 28 to provide enhanced containment and leakage-resistance.

Specifically, each side marginal portion 34 includes a first outer segment 36 juxtaposed and joined to the underlying backsheet 26 laterally outwardly of the side edge of absorbent panel 28. Each side marginal portion 34 further includes a second, intermediate segment 38 adjacent the first segment 36 and positioned generally inwardly thereof. A third, standing gather segment 40 of each side marginal portion is positioned adjacent the second, intermediate segment, and is configured to provide one of the two inner standing gather constructions of the garment.

To this end, each standing gather segment 40 includes an overturned free edge to thereby define a sleeve portion 42. In accordance with the illustrated embodiment, it is presently preferred that the free edge of each standing gather be overturned inwardly toward the longitudinal centerline of the absorbent garment, particularly when the longitudinal end portions of each standing gather are secured inwardly, as will be further described.

The sleeve portion 42 of each standing gather segment 40 is secured in its overturned position by suitable bonding of the segment to itself, with a spray adhesive 44 being presently preferred. In order to achieve the desired gathering effect for each standing gather segment, at least one elastic element 46 extends within the sleeve portion 42 along at least the crotch area 16 of the garment. While various techniques may be employed, it is presently preferred that the standing gather elastic element 46 be applied to the nonwoven material from which the side marginal portion 30 is formed by securing the elastic to the nonwoven material with the elastic in an extended or stretched condition. The adhesive 44 is preferably employed for both securing the elastic element 46 to the standing gather segment 40, as well as for formation of sleeve portion 42.

In the illustrated embodiment, including the hourglass-shaped absorbent panel 28, each of the first outer segments 36 and the third standing gather segment 40 are of a substantially constant dimension throughout the length of the garment 10. In contrast, each second intermediate segment 38 varies in dimension, being relatively narrow at the crotch area 16 of the garment, and relatively wider at each of the front and rear waist portions 12 and 14 whereat the absorbent panel extends beneath each intermediate segment.

With further reference to FIG. 3, any of a variety of techniques may be employed for securing the first segment 36 of each side marginal portion 34 to the associated backsheet 26. It is presently preferred that a spray adhesive 48 be used for this purpose. It is also presently preferred that one or more leg elastic elements be provided in this region to thereby elasticize each leg opening, generally at each leg cut-out 18, for the desired fit and containment. In the illustrated embodiment, a pair of leg elastic elements 50 are provided between first segment 36 and backsheet 26, with the spray adhesive 48 acting to secure the elastic elements in position. In accordance with known formation techniques, elastic elements 50 are integrated with the associated backsheet and topsheet assembly in an extended or stretched condition, whereby the absorbent garment 10 is effectively gathered to form an elastically extensible structure.

As illustrated, opposite side edges of central portion 32 of topsheet assembly 30 are respectively joined to the side marginal portions 34. Specifically, each of the side edges of the central portion 32 is joined to the respective one of the side marginal portions generally at the juncture of the second and third segments 38 and 40 of the side marginal portion. While standard gluing methods can be used, it is presently preferred that this be achieved by the provision of a sonic bond 52 which extends longitudinally of the garment (generally as illustrated in phantom line in FIG. 2) thereby integrating the topsheet assembly.

Significantly, this relative disposition of the sonic bond 52 acts to space the side edge of the central portion 32, at least in the crotch area 16, from the backsheet 26 of the garment by the dimension of the respective second intermediate segment 38. This preferred configuration has been found to desirably avoid formation of trough-like regions just inwardly of the standing gather segments 40, thereby acting to avoid collection of liquid in such regions, which collection is believed to contribute to leakage of the garment.

In the illustrated embodiment, the absorbent panel 28 is positioned substantially between second and third segments 38 and 40 of the side marginal portions 30, at least in the crotch area 16. While such an arrangement is desirable, normal manufacturing tolerances and variances can make it difficult to precisely align the bond 52 with the edge of the panel 28. Additionally, the nonwoven fabric from which central portion 32 is typically formed exhibits some extensibility, which can permit the base of each standing gather segment 40 to shift laterally outwardly.

Since it is most preferred that to avoid creating trough-like regions adjacent the standing gathers, the bonds 52 can be positioned generally at or just inwardly of the side edges of the panel 28. Even though portions of the panel may thus extend beneath the third standing gather segments 40, formation of the side marginal portions 30 from material exhibiting significant hydrophobicity has been found to abate leakage of liquid from those panel portions which extend beneath the standing gather elements. As will be appreciated, use of a relatively thin absorbent panel 28, and the desire to avoid forming trough-like regions adjacent the standing gathers, calls for the preferred disposition of bonds 52 generally on top of such a thin panel.

As shown in FIG. 1, the hourglass shape of absorbent panel 28, including the provision of laterally extending ear portions in the front and rear waist portions 12 and 14, results in the ear portions of the absorbent panel extending beneath the second intermediate segment 38 of each side marginal portion in the waist portions of the garment. However, the nonwoven material from which the marginal portions are formed is preferably selected to exhibit sufficient hydrophobicity so as to substantially preclude the possibility of liquid from the ear portions of the absorbent panel moving toward the wearer of the garment. Additionally, materials which exhibit the desired hydrophobicity have further been found to provide enhanced strength, and stretch and tear resistance, thus promoting secure and convenient use of the tape tabs 20.

Referring to FIG. 4, the preferred configuration of each of the front and rear waist portions of the garment 10 is illustrated. As will be observed, it is preferred that the longitudinal end portions of each of the standing gather segments 40 of the side marginal portions 30 be secured inwardly to the central portion 32 of the topsheet assembly. To this end, a sonic bond 54 is preferably provided at each of the longitudinal end portions of the standing gather segments (see FIG. 2). As is also illustrated in FIG. 4, it is presently preferred that the garment 10 be provided with front and rear waist elastic elements 56, which may comprise suitable foam elastic material for enhanced fit and comfort.

As noted above, it is preferred that the free edge of each standing gather segment 40 be overturned inwardly toward the garment centerline, particularly when the end portions of the standing gather segments 40 are secured inwardly as shown in solid line in FIG. 4. This is aesthetically preferred since the edge of the gathered material at sleeve portion 42 is generally concealed, and also acts to avoid the material edge contacting the wearer of the garment.

However, the standing gather segments can be otherwise configured. For example, at least one of the longitudinal end portions of each standing gather segment 40 can be secured outwardly to at least one of the respective first and second segments 36, 38, as illustrated in phantom line in FIG. 4, in which event it can be desirable to have the free edge of each standing gather segment be overturned outwardly away from the garment centerline, as shown. It can be particularly desirable to secure the rearward longitudinal portions of the standing gather segments inwardly (to central portion 32) and the forward longitudinal portions outwardly (to at least one of the first and second segments 36, 38), thereby forming a pouch-like construction in the forward portion of the garment (which portion ordinarily receives the most liquid during use).

As will be appreciated, a wide variety of materials may be employed for fabrication of the composite topsheet assembly 30. Nonwoven fabric materials are presently preferred, with the side marginal portions 34 preferably comprising nonwoven materials exhibiting a relatively high degree of hydrophobicity. One suitable material for the side marginal portions is spunbonded polypropylene nonwoven fabric having a basis weight in the range of about 0.3 to 0.8 ounces/square yard and a bond area in the range of about 7% to 20%, with a basis weight of about 0.5–0.6 ounces/square yard and an 18% bond area being particularly preferred. When untreated, this material exhibits the desired degree of hydrophobicity. One commercially available material of this type is available from Fiber Web of America, Greenville, S.C., under the product designation Unicorn Celestra TM.

The central portion 32 of the composite topsheet assembly may also comprise a polypropylene nonwoven fabric having a basis weight and bond area as described above for side marginal portions 34. While the central portion 32 of an absorbent garment embodying the present invention can be selected to exhibit relatively high or relatively low liquid impermeability, it is presently preferred that the central portion 32 be selected to exhibit significantly greater hydrophilicity, and thus greater liquid permeability, than side portions 34. To this end, polypropylene nonwoven material such as described above is ordinarily treated with a surfactant to achieve the desired hydrophilicity Alternately, a hydrophobic fabric having apertures to permit liquid passage therethrough may be employed.

FIG. 5 illustrates a modified embodiment of the present disposable diaper 10, which in most respects is in accordance with the previously-described embodiment. In this illustrated construction, however, a modified absorbent panel 28 includes a relatively narrow portion, defined by panel cut-outs 28', which relatively narrow portion extends along part of the crotch area 16 extending between front and rear waist portions 14 and 12. By this construction, the bond 52 between the central topsheet portion 32 and each respective side marginal portion of the topsheet assembly is positioned generally at a respective upper edge portion of the absorbent panel generally in a plane of an upper surface of the absorbent panel through at least a portion of the crotch area 16 of the absorbent garment. The relatively narrow panel portion defined by panel cut-outs 28' enhances fit of the absorbent garment when put in place on a wearer such that the crotch region 16 extends between the legs of the wearer.

In summary, the present construction has been found to provide desirably enhanced containment characteristics. By the arrangement of the bonds at 48 and 52, plus the use of the preferred hydrophobic material for side marginal portions 34, the marginal portions function in the nature of shields at the sides of the absorbent panel 28 to abate leakage. Additionally, the bonding of the marginal portions to the backsheet avoids the creation of gaps or the like through which leakage might otherwise leak from the construction.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. A disposable absorbent garment, comprising:
   a backsheet;
   an absorbent panel positioned on top of said backsheet; and
   a composite three-component topsheet assembly positioned on top of said absorbent panel, said topsheet assembly comprising a central portion, and a pair of side marginal portions positioned at respective opposite sides of said central portion,
   each said side marginal portion including, in a crotch area of said absorbent garment, a plurality of segments including a first segment juxtaposed and bonded to said backsheet laterally outwardly of said absorbent panel, a second intermediate segment adjacent said first segment, and a third standing gather segment adjacent said second intermediate segment,
   said third standing gather segment of each said side marginal portion of said topsheet assembly including an overturned free edge to thereby define a sleeve portion, said garment including at least one elastic element extending within each said sleeve portion along at least the crotch area of said garment; and
   at least one elastic element positioned between each said first segment of each said side marginal portion of said composite topsheet assembly and the backsheet at least in the crotch area of said absorbent garment,
   said central portion of said topsheet assembly being joined to each said side marginal portion with bond means positioned at a respective juncture of said second intermediate segment and said third standing gather segment in spaced relationship to said overturned free edge, so that the said central portion is joined to the respective side marginal portion with said bond means positioned in spaced relationship, by the respective second intermediate segment, to said backsheet, whereby said bond means is free from attachment to said backsheet and is positioned generally at a respective upper edge portion of said absorbent panel generally in a plane of an upper surface of said absorbent panel, at least along a portion of the length of the crotch area of said absorbent garment.

2. A disposable absorbent garment in accordance with claim 1, wherein
   said central portion of said composite topsheet assembly exhibits greater hydrophilicity than said side marginal portions of said assembly.

3. In a disposable absorbent garment in accordance with claim 1, wherein
   opposite longitudinal end portions of said standing gather segment of each said side marginal portion are secured inwardly to said central portion of said composite topsheet assembly.

4. A disposable absorbent garment in accordance with claim 1, wherein
   each said side marginal portion comprises hydrophobic spunbonded polypropylene fabric material having a basis weight of 0.3–0.8 ounces/square yard and a bond area in the range of about 7% to 20%.

* * * * *